United States Patent [19]

Sampino et al.

[11] Patent Number: 5,674,480
[45] Date of Patent: Oct. 7, 1997

[54] MULTIPLE UTILITY HAIR-CARE PRODUCT

[76] Inventors: Andrew F. Sampino, 159-11 78th St., Howard Beach, N.Y. 11414; Anthony F. Sampino, 46 Rose Ave., Great Neck, N.Y. 11021

[21] Appl. No.: 559,132

[22] Filed: Nov. 17, 1995

Related U.S. Application Data

[63] Continuation-in-part of Ser. No. 249,258, May 25, 1994, abandoned.

[51] Int. Cl.$^6$ .............................. A61K 7/06; A61K 7/11
[52] U.S. Cl. ......................... 424/70.13; 424/70.17; 424/DIG. 2
[58] Field of Search ............... 424/70.13, 70.17, 424/DIG. 2

[56] References Cited

U.S. PATENT DOCUMENTS

| | | | |
|---|---|---|---|
| 4,134,412 | 1/1979 | Gross et al. | 132/7 |
| 4,202,881 | 5/1980 | Gross et al. | 424/70 |

*Primary Examiner*—Sallie M. Gardner
*Attorney, Agent, or Firm*—Goldstein & Associates

[57] ABSTRACT

A method of using a multipurpose hair-care product utilizing the active ingredient chitosonium pyrrolidone carbonxylate which is primarily derived from shrimp and other shell fish yielding a product having improved cutting lotion, memory lock, straightening and relaxing characteristics. The method comprises applying the product to the hair after shampooing and drying the hair.

3 Claims, 1 Drawing Sheet

MULTIPLE UTILITY HAIR-CARE PRODUCT

This application is a continuation-in-part of application Ser. No. 08/249,258, now abandoned, filed May 25, 1994.

BACKGROUND OF THE INVENTION

The invention relates to hair-care and hair-spray compositions especially formulated for use in low organic volatile systems.

The invention further relates to a polymeric hair-care product which comprises an aqueous-based solution process for making natural fixatives and water-based hair spray formulations which meet VOC (volatile organic compounds) standards.

The invention is an aqueous, hydroalcohol, non-aerosol, hair-care compositions which contain a surface active agent or agents to reduce the surface and interfacial tension of the water or hydroalcoholic phase of the composition thus providing a uniform, fine spray pattern which dries rapidly.

Human hair commonly becomes soiled due to sebum secreted naturally by the scalp as well as soil and other atmospheric contaminants which accumulate on the hair. The build-up of sebum causes the hair to have a greasy, dirty feel, poor manageability, and an unattractive appearance. Shampooing the hair cleans by removing from the hair excess oil, sebum, atmospheric contaminants, and residues resulting from the usage of a variety of hair styling products such as sprays, gels and mousses. While most shampoos are very effective for cleansing the hair, they have the undesirable effect of leaving the hair in an unmanageable state. Thoroughly cleansed hair is extremely difficult to comb in both wet and dry states because the individual hair fibers, stripped of important oils and moisture, tend to tangle with each other. Also, thoroughly cleansed hair in the dry state has undesirable electronic properties in a relatively low humidity atmosphere which cause the hair to "fly away," thereby further reducing the overall manageability of the hair.

A variety of means have been developed to alleviate the problems associated with after-shampooed hair. These range from using after-shampoo hair conditioner to including hair conditioning agents directly in the shampoo compositions. After-shampoo hair conditioners are easily formulated but must be applied in a separate step following the shampooing. This, of course, is time-consuming and inconvenient. Among the most effective hair conditioners are those that contain cationic surfactant such as long chain diakyl dimonium chlorides.

To address these problems, manufacturers of hair care products have attempted to produce hair shampoo/conditioners which utilize shellfish derived Chitosonium pyrrolidone carboxylate, in attempt to take advantage of the moisturizing effect said chitosan derivatives have on keratinous material. U.S. Pat. No. 4,202,881 to Gross discloses such a hair conditioning composition comprising chitosan derivatives, which contemplates the use of such composition in conjunction with conventional shampoo/conditioners which are intended to be rinsed clean from the hair after use and hence combat the above mentioned problems inherent in hair care. It is not contemplated, as is the case with the instant invention, to be left to remain in the hair during and after styling as a stand-alone hair styling aid. Similarly, U.S. Pat. No. 4,134,412 to Gross discloses the use of a chitosan derivative based composition for setting hair. Said composition is not used as a post-shampooing stand-alone hair styling aid to combat the moisture stripping characteristics of traditional shampooing as is intended by the instant invention, but rather is used as a setting agent to be applied to the hair prior to the hair being set by means of a heat drier.

Hair-care and hair-spray compositions must meet a number of functional requirements. These include providing good holding ability and curl retention without giving a harsh, brittle feeling to the hair. Even under humid conditions there must be good hold and curl retention. Another requirement is that the composition be capable of being removed upon washing the hair at the time of shampooing. Additionally, the compositions must include the properties of low stickiness, good combing characteristics and a lack of powdering or flaking. The aqueous, chitosin derived composition of the instant invention fulfills all of these requirements.

Furthermore, the composition of the instant invention satisfies environmental concerns and legislation requiring product reformation to prevent damage to the environment. Organic solvent-based sprays must, at least in part, now be substituted by water systems. Levels of organic propellants present in these water systems must also be adjusted to relatively low levels. Present hair sprays found in the art, however, generally contain large amounts of alcohol above mandated VOC (volatile organic compounds) standards.

As a result of attempted compliance with these constraints, certain problems have arisen. Water-dispersed systems are slow to dry and result in wetness on the hair and an undesirable sensation of coolness that imparts a chill. Quite significantly there is also great difficulty in styling the hair.

Resins, which have been utilized and formulated in a water-dispersed system, tend to have weak holding power. While some products utilize resins which possess good setting or holding capabilities, removability from the hair proves to be quite difficult because these resins are not water soluble.

Alcohol, which often functions as a solvent for the resin fixative components of the above mentioned formulations provides high curl retention, low drying time and low curl droop properties for the user. Unfortunately, the addition of water and the minimization of alcohol in hair spray compositions in attempts to meet VOC requirements causes said hair sprays to lose alcohol as the spray reaches the hair, thus becoming even more aqueous and losing more of its desired beneficial qualities. As the water level increases, so does the surface and interfacial tension, which results in poor wetting and large droplets on the hair. These droplets dry very slowly, particularly as the water content of the composition is increased during dry down, which is objectionable in use because of tack.

Accordingly, it is desired to provide an aqueous based hair spray compositions which meet VOC requirements without sacrificing advantageous user properties.

Accordingly, it is a particular objective of this invention to provide a water and chitosin derivative based hair care composition which satisfies VOC standards yet which forms uniform, fine spray patterns which dry rapidly to give effective curl retention, low curl droop, non-tackiness, luster, sheen, low comb drag and a clean feel on the hair without comb residue.

Numerous innovations for a multiple utility hair-care product have been provided in the prior art that are adapted to be used. Even though these innovations may be suitable for the specific individual purposes to which they address, they would not be suitable for the purposes of the present invention as heretofore described.

SUMMARY OF THE INVENTION

The present invention discloses a new use of an active ingredient in hair products, namely Chitosonium pyrrolidone carbonxylate (the active ingredient). The active ingredient is natural, is derived from shell-fish such as shrimp, and is mixed at approximately 0.01% to 2% in water, the preferred range being 0.3–0.5%

The present invention possesses several new and beneficial characteristics. First and most importantly, the composition described herein provides a quality known as "memory lock", in that it is extremely effective in setting hair and allowing it to maintain position. After application of the product, if you pull on a curl and then release it, said curl will bounce back.

Furthermore, the composition acts as a straightener and relaxer. Similar to the memory lock feature, the relaxer yields a new method by which hair-care and hair treatment is achieved, hence, producing a novel product with unique unexpected results in the field of hair-care products. The hair-care product in the present invention may be sprayed by pump or aerosol, or applied directly to the hair.

Finally, the invention may be utilized as a cutting lotion since the composition makes hair slippery as well as makes combing hair easy to prepare for cutting. It allows a hair-cutting razor or scissors to effortlessly slice through the hair without resistance. Application of this product prior to a hair cut also prevents wear to scissors, allowing them to maintain their sharpness for a longer period of time To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

Figure 1:
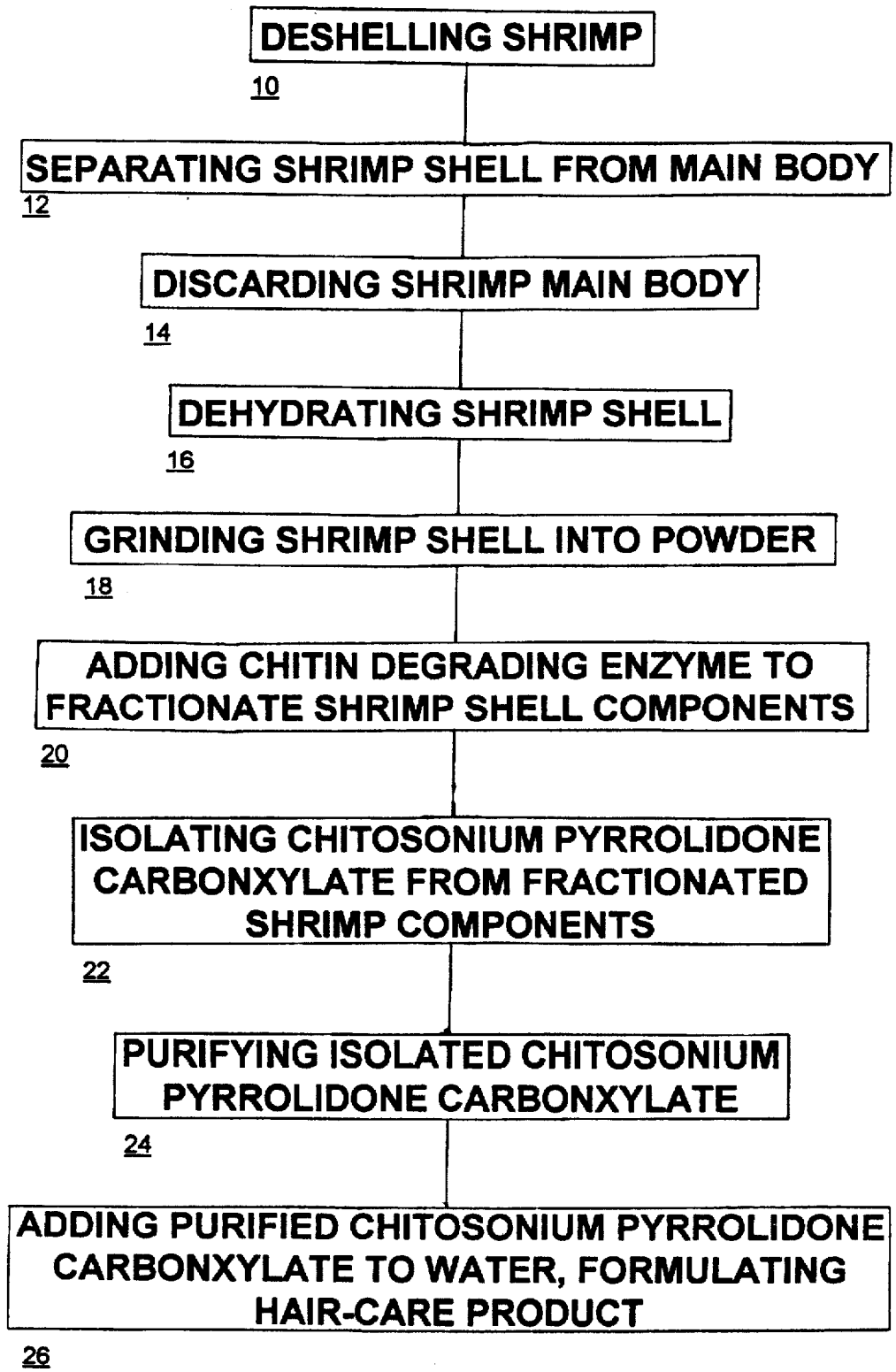
FIG. 1 is a is a diagrammatic flow chart of a method by which chitosonium pyrrolidone carboxylate is extracted from shrimp.

DETAILED LIST OF REFERENCE NUMERALS UTILIZED IN THE DRAWING 10-de-shelling shrimp 10 by inserting a de-shrimping tool between shrimp main body and shrimp shell, thus, cracking and simultaneously separating shrimp shell from main body 12-separating shrimp shell from main body 12 by securely adhering shrimp shell in a stable position and simultaneously adhering shrimp main body in a movable position such that when said shrimp main body and said shrimp shell are pulled in opposite directions both shell and main body separate 14-discarding shrimp main body 14

16-dehydrating shrimp shell 16 by desiccating said shell utilizing common methods to one skilled in the art such as low intensity heat for a prolonged time period and/or use of dehydrating materials such as salt and anhydrous silicone crystals 18-grinding shrimp shell into powder 18 utilizing common methods to one skilled in the art such as mortar and pestle and like equivalents 20-adding chitin degrading enzymes 20 such as chitinaze which enzymatically fractionates shrimp shell into its individual components 22-isolating chitosonium pyrrolidone carboxylate from fractionated shrimp components 22 utilizing common methods to one skilled in the art such as absorbent techniques such as lectin absorbent and monoclonal antibodies and/or elusion column 24-purifying isolated chitosonium pyrrolidone carboxylate 24 utilizing common methods to one skilled in the art such as absorbent techniques such as lectin absorbent and monoclonal antibodies and/or elusion column 26-adding purified chitosonium pyrrolidone carboxylate to water, formulating hair-care product 26 utilizing common methods to one skilled in the art such as homogenization

DETAILED DESCRIPTION OF THE PREFERRED EMBODIMENTS

Referring to FIG. 1 which is a diagrammatic flow chart of a method by which chitosonium pyrrolidone carboxylate is extracted from shrimp, the following steps are illustrated: de-shelling a shrimp 10 by inserting a de-shrimping tool between said shrimp main body and shrimp shell, thus, cracking and simultaneously separating said shrimp shell from main body; separating shrimp shell from main body 12 by securely adhering shrimp shell in a stable position and simultaneously adhering shrimp main body in a movable position such that when said shrimp main body and said shrimp shell are pulled in opposite directions both shell and main body separate; discarding shrimp main body 14; dehydrating shrimp shell 16 by desiccating said shell utilizing common methods to one skilled in the art such as low intensity heat for a prolonged time period and/or use of dehydrating materials such as salt and anhydrous silicone crystals; grinding shrimp shell into powder 18 utilizing common methods to one skilled in the art such as mortar and pestle and like equivalents; adding chitin degrading enzymes 20 such as chitinaze which enzymatically fractionates shrimp shell into its individual components; isolating chitosonium pyrrolidone carboxylate from fractionated shrimp components 22 utilizing common methods to one skilled in the art such as absorbent techniques such as lectin absorbent and monoclonal antibodies and/or elusion column; purifying isolated chitosonium pyrrolidone carboxylate 24 utilizing common methods to one skilled in the art such as absorbent techniques such as lectin absorbent and monoclonal antibodies and/or elusion column; and adding purified chitosonium pyrrolidone carboxylate to water, formulating hair-care product 26 utilizing common methods to one skilled in the art such as homogenization.

Additional non-essential ingredients such as preservatives like parabin (methyl, propyl or butyl), DMDM hydantons, fragrances, emulsifiers, colors, and surfactants (shampoo) may be added prior to said homogenization step.

It will be understood that each of the elements described above, or two or more together, may also find a useful application in other types of constructions differing from the type described above.

Advantageously, the product may be applied to wet or dry hair either directly or by aerosol or pump spray. The product may be applied in the hair immediately prior to cutting. When thus applied, the hair develops a slippery texture which allows effortless cutting by either scissors or a razor. The preferred method of application involves shampooing the hair, towel drying the hair, and then applying the product by spraying it on the hair. The hair is then ready for cutting or styling.

The product may also be applied to hold a hair style. For such a purpose, the product is applied to styled hair. Contrary to expectations, the styled hair will maintain its position, and will reveal its "memory lock" feature. The memory lock feature is simply that a curl pulled and released will return to its styled position.

The method of application, involves spraying the composition directly onto the dry, styled hair. Thus, according to the inventive method, the composition is used as a substitute for "hair sprays" or finishing sprays, which are applied to the hair well after, shampooing, conditioning, setting, and styling, to hold the hair style. This distinction is important, since previously it was not known that the active ingredient could function as a stand-alone hair spray substitute. Although similar chemicals may have been used along with other ingredients in shampooing and conditioning products used on wet hair, they are intended to be rinsed from the hair immediately. It is contrary to the known properties of the active ingredient of the invention that it would be suitable to be left in the hair for a prolonged period. Thus it is contrary to expectations that the active ingredient, chitosonium pyrrolidone could be used as a styling aid, a hair spray, or as a finishing spray.

In addition, the product may be utilized as a straightener or relaxer. The product is sprayed onto the hair while combing through the hair. The hair will maintain its straightened or relaxed position. Once again, it is preferable to shampoo and towel dry the hair prior to application of the product.

In conclusion, herein is presented a novel use for chitosonium pyrrolidone carbonxylate in a simple water solution, in a hair care product. The solution may be applied directly to the hair after styling, to hold the hair style.

What is claimed is:

1. A method of setting hair using a multiple utility hair-care product consisting essentially of 0.01–2% chitosonium pyrrolidone carbonxylate in water comprising applying the product to the hair.

2. The method as recited in claim 1, wherein the recited method is preceded by the steps of:

shampooing the hair;

drying the hair, and wherein the step of applying the product to the hair further comprises spraying the product onto the hair.

3. The method of using a multiple utility hair care product as recited in claim 1, wherein the step of applying the product further comprises spraying the product onto the hair using a device selected from a pump and an aerosol dispenser.

* * * * *